(12) United States Patent
Miller et al.

(10) Patent No.: US 7,965,820 B2
(45) Date of Patent: Jun. 21, 2011

(54) FIDUCIAL MARKER FOR CORRELATING IMAGES

(75) Inventors: Lisa Marie Miller, Rocky Point, NY (US); Randy J. Smith, Wading River, NY (US); John B. Warren, Port Jefferson, NY (US); Donald Elliott, Hampton Bays, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 137 days.

(21) Appl. No.: 12/191,525

(22) Filed: Aug. 14, 2008

(65) Prior Publication Data

US 2009/0048510 A1    Feb. 19, 2009

Related U.S. Application Data

(60) Provisional application No. 60/956,522, filed on Aug. 17, 2007.

(51) Int. Cl.
*G01N 23/223* (2006.01)
*G01N 23/04* (2006.01)

(52) U.S. Cl. .............................. 378/164; 378/44; 378/63

(58) Field of Classification Search .................... 378/63, 378/164, 206, 44
See application file for complete search history.

(56) References Cited

U.S. PATENT DOCUMENTS

| | | | |
|---|---|---|---|
| 4,371,806 A | 2/1983 | Bintig et al. | 313/101 |
| 5,178,146 A | 1/1993 | Giese | 128/653 |
| 7,027,644 B1 | 4/2006 | Kim et al. | 382/165 |

OTHER PUBLICATIONS

Miller, Lisa M., et al., "Synchrotron-based infrared and X-ray imaging shows focalized accumulation of Cu and Zn co-localized with β—amyloid deposits in Alzheimer's disease", J. Structural Biology, 155, 30-37 (published online Nov. 14, 2005).
Miller, Lisa M., et al., "Development and applications of an epifluorescence module for synchrotron x-ray fluorescence microprobe imaging", Review of Sci. Instr., 76: 066107 (2005) (published online Jun. 7, 2005).
Miller et al., et al., "A new sample substrate for imaging and correlating organic and trace metal composition in biological cells and tissues", Anal. Bioanal. Chem., 387(5):1705-15 (2007) (e-published Nov. 18, 2006).

*Primary Examiner* — Edward J Glick
*Assistant Examiner* — Thomas R Artman
(74) *Attorney, Agent, or Firm* — Dorene M. Price

(57) ABSTRACT

The invention relates to a fiducial marker having a marking grid that is used to correlate and view images produced by different imaging modalities or different imaging and viewing modalities. More specifically, the invention relates to the fiducial marking grid that has a grid pattern for producing either a viewing image and/or a first analytical image that can be overlaid with at least one other second analytical image in order to view a light path or to image different imaging modalities. Depending on the analysis, the grid pattern has a single layer of a certain thickness or at least two layers of certain thicknesses. In either case, the grid pattern is imageable by each imaging or viewing modality used in the analysis. Further, when viewing a light path, the light path of the analytical modality cannot be visualized by viewing modality (e.g., a light microscope objective). By correlating these images, the ability to analyze a thin sample that is, for example, biological in nature but yet contains trace metal ions is enhanced. Specifically, it is desired to analyze both the organic matter of the biological sample and the trace metal ions contained within the biological sample without adding or using extrinsic labels or stains.

38 Claims, 7 Drawing Sheets

FIDUCIAL MARKER FOR CORRELATING IMAGES

This application claims priority under 35 U.S.C. §119(e) to U.S. Provisional Patent Application No. 60/956,522 which was filed on Aug. 17, 2007, the entirety of which is incorporated by reference as if fully set forth in this specification.

The present invention was made with government support under Contract No. DE-AC02-98CH10886 awarded by the U.S. Department of Energy. The United States government has certain rights in the invention.

FIELD OF THE INVENTION

The invention relates to a fiducial marker having a grid that is used to correlate and view images produced by different imaging modalities. More specifically, the invention relates to the fiducial marking grid having a grid pattern used to produce viewing and analytical images that are overlaid and correlated to view a light path or to image different imaging modalities.

BACKGROUND OF THE INVENTION

Many disease processes involve alterations in the chemical makeup of tissue. Synchrotron-based infrared (IR) and x-ray fluorescence microscopes (XRFM) are becoming increasingly popular for imaging both organic and trace metal compositions of biological cells and tissues, respectively, without the need for extrinsic labels or stains. Coupled with visible light microscopy, these techniques can be used to correlate conventional histological structure to organic and trace-element composition. Fourier transform infrared microspectroscopy (FTIRM) provides chemical information on the organic components of a material at a diffraction-limited spatial resolution of 2-10 µm in the mid-infrared region. FTIRM provides chemical information on the organic components of a tissue such as proteins, lipids, nucleic acids, and carbohydrates. FTIRM is very sensitive to protein secondary structure in tissue as well, where the frequency of the Amide I band, assigned to the amide ($>C=O$) backbone of the protein, has a different absorption maximum for $\alpha$-helical ($\sim$1655 cm$^{-1}$), $\beta$-sheet ($\sim$1630 cm$^{-1}$), and extended coil ($\sim$1645 cm$^{-1}$) proteins. For example, the structure of misfolded protein aggregates has been identified in the brain tissue of Alzheimer's disease patients and infectious prion proteins have been characterized in scrapie, a sheep's form of mad cow disease. In addition to protein structure, variations in bone composition have been observed in osteoporosis, osteopetrosis, and osteoarthritis. In heart disease, altered lipid and collagen content and structure in the myocardium have been seen, which were partially normalized by losartan treatment.

Synchrotron x-ray fluorescence (SXRF) microprobe is used to probe trace elements with sensitivities, for example, in the sub-mg kg$^{-1}$ range and a spatial resolution similar to FTIRM (2-10 µm). Because of the low power deposition that x-rays provide and the ability to conduct the analyses in air, these analyses can be done non-destructively on a much wider array of sample types, especially, relatively fragile biological samples. For example, the alterations in trace metals such as Fe, Cu, and Zn have been observed in neurological diseases such as Parkinson's disease, amylotrophic lateral sclerosis, Alzheimer's disease, and prion diseases and cancer. Environmental toxins have also been imaged in human tissue, such as elevated levels of methyl mercury and lead in hair.

In many disease states and environmental contamination, both the organic and metal ion compositions are altered. Therefore, in order for all imaging techniques applied to a single sample to be most beneficial as analytical tools, it is desirable to combine their results, which requires precise overlap of the visible, IR and x-ray images. Yet most of the abovementioned studies utilize only a fraction of the available tools, and therefore, do not examine every aspect of the disease. As a result, there can be pertinent information that is missed regarding the relationship between the alterations of the organic and metal contents, which plays a vital role in understanding the origins or other aspects of the diseases.

One means of remedying this situation is to register one image space to another image space. The goal of registering two (or more) separate and arbitrarily oriented images is to align the coordinate systems of the two images such that any given point in the scanned biological sample is assigned identical addresses in both images. The calculation necessary to register the two coordinate systems requires knowledge of the coordinate vectors of at least three points (for a 3-D image space) in the two systems. These points are referred to as "fiducial points" or "fiducials," and the fiducials used are the geometric centers of markers, which are referred to as "fiducial markers". The fiducials are used to correlate image space to another image space, or to correlate image space to a physical space. The fiducial markers provide a constant frame of reference visible in a given imaging mode to make registration possible.

One problem recognized as extant is the provision of fiducials capable of use with more than one imaging modality. For example, in the case of computed tomographic imaging (CT) and magnetic resonance imaging (MRI), the bony structure information from a CT scan could be integrated with soft tissue anatomical information from an MRI scan. MRI and x-ray CT images are digital images that are formed point by point. Collectively the points are called picture elements, or pixels, and are associated with an intensity of light emitted from a cathode ray tube, or are used to form an image on film. The manner in which the intensity of any given pixel is altered or modulated varies with the imaging modality employed. In x-ray CT, the modulation is, in general, a function of the number of electrons per unit volume being scanned. While in MRI, the parameters largely influencing this modulation are the proton spin density and longitudinal and transverse relaxation times T1 and T2, which are also known as the spin-lattice and spin-spin relaxation times, respectively.

In another example, XRFM is performed by focusing a small x-ray beam (about 10 microns square) on a sample and raster-scanning the sample through the beam to collect an x-ray fluorescence spectrum at each pixel. By integrating the fluorescence intensity of a particular trace metal at each pixel, a metal-distribution image can be generated. Currently, with XRFM, a light microscope objective is used to view the sample. However, the light microscope objective is unable to visualize the actual location of the x-ray beam.

In constructing a fiducial marker, it must be taken into consideration that an object that can be imaged under one imaging modality will not necessarily be imageable under another modality. Another reason for precise overlap of images is in the case of differing reflective optics such that their corresponding images are not correlated. Specifically, with XRFM, in which images are not correlated, visible light illumination and sample magnification is performed through a glass microscope objective. The visible light image and x-ray beam must be precisely overlapped in order for the XRFM image to align with the light microscope image. This can be a challenge as any motion in the x-ray beam or the visible light optics can prevent precise overlapping. Further, the lack of alignment in the images is not detected during data analysis and collection because the x-ray beam is not visible.

The ability to image with at least one imaging technique and correlate that image with a light microscope image would be particularly useful because images derived from different imaging modalities could then be registered and analytical tools such as, for example, XRFM can be used more efficiently when coupled with for example FTIRM. Therefore, there remains a need for fiducial markers that can be used to correlate at least one analytical image produced by at least one imaging modality with a viewing image of a microscope objective or with a second analytical image. To achieve this end, the present invention relates to a fiducial marking grid which can correlate at least one analytical image with a light microscope image or with a second analytical image.

SUMMARY OF THE INVENTION

The invention relates to a fiducial marker for correlating a first analytical image produced by a first imaging modality with at least one second image produced by at least one second modality. The ability to make the correlation between the two images enhances the ability to analyze a thin sample. The fiducial marker of the present invention comprises a sample substrate having a surface, and a marking grid composed of a metallic material that is substantially free of contaminants that would interfere with the desired measurement of ppm (parts per million) concentrations of for example trace metal ions in the thin sample. The marking grid has a grid pattern that is coated on the surface of the substrate. The grid pattern is imageable by the first imaging modality and at least one second modality. The second modality can be either a viewing modality or an analytical modality. The first analytical image overlaps the at least one second image to achieve the correlation. Thus, the fiducial marker can be used to correlate the first analytical image produced by an x-ray beam of an x-ray fluorescence microprobe with the second modality that is a light microscope objective for producing a viewing image of the thin sample. The grid pattern is imageable by x-ray fluorescence microprobe and the light microscope objective where the x-ray beam cannot be visualized by the light microscope objective.

In another method of the present invention, the first analytical image produced by x-ray fluorescence microprobe is correlated with a viewing image produced by a viewing modality such that the two grid patterns can be co-registered to analyze a thin sample. In this method, the first image grid pattern and a viewing image grid pattern are produced by the x-ray fluorescence microprobe and the viewing modality, respectively. Similarly, the two grid patterns are co-registered to precisely overlap the first image grid pattern with the viewing image grid pattern and analyze the thin sample.

The present invention also includes the marker and the method of viewing a first analytical image of a thin sample using an x-ray fluorescence microprobe having an x-ray beam that cannot be visualized by a light microscope objective. The marking grid is imageable by the x-ray fluorescence microprobe and by the light microscope objective. The first analytical image grid pattern is produced by the x-ray fluorescence microprobe and the viewing image grid pattern is produced by the light microscope objective. The viewing image is correlated with the x-ray beam of the x-ray fluorescence microprobe by co-registering the two grid patterns.

In addition, the present invention includes the fiducial marker and the method of its use to correlate a first analytical image produced by a first imaging modality with at least one second analytical image produced by at least one second imaging modality for analysis of the thin sample. Similarly, the fiducial marker comprises the substrate with the grid pattern coated thereon. However, in this case, the grid pattern has at least two different pattern thicknesses, and is imageable by the first imaging modality and by the at least one second imaging modality. The first analytical image overlaps the at least one second analytical image to achieve the correlation.

The present invention also includes the marker and the method of correlating a viewing image produced by a viewing modality, a first analytical image produced by x-ray fluorescence microprobe with at least one second analytical image produced by at least one second imaging modality comprising the steps of patterning a marking grid on a surface of a sample substrate that is imageable by the viewing modality, by x-ray fluorescence microprobe and by the at least one second imaging modality. The marking grid has at least two pattern thicknesses. A viewing image grid pattern is produced by the viewing modality, a first image grid pattern is produced by the x-ray fluorescence microprobe and at least one second image grid pattern is produced by the at least one second imaging modality. All of the image grid patterns, namely the viewing image grid pattern, the first image grid pattern, and the at least one second image grid pattern, are co-registered to achieve the correlation and analysis of the thin sample.

BRIEF DESCRIPTION OF THE DRAWINGS

FIG. 9 (bottom) illustrates a gold x-ray fluorescence image of the sample substrate shown in FIG. 9 (top), having a grid pattern thereon where the sharpness of the edge is 2-3 µm. Scale bar is 15 µm in both FIG. 9 (top) and FIG. 9 (bottom).

FIG. 11 (bottom) illustrates a single layer chromium x-ray fluorescence image of the sample substrate shown in FIG. 11 (top), having a grid pattern thereon where the sharpness of the edge is 2-3 µm. Scale bar is 15 µm in both FIG. 11 (top) and FIG. 11 (bottom).

DETAILED DESCRIPTION OF THE INVENTION

Figure 1:
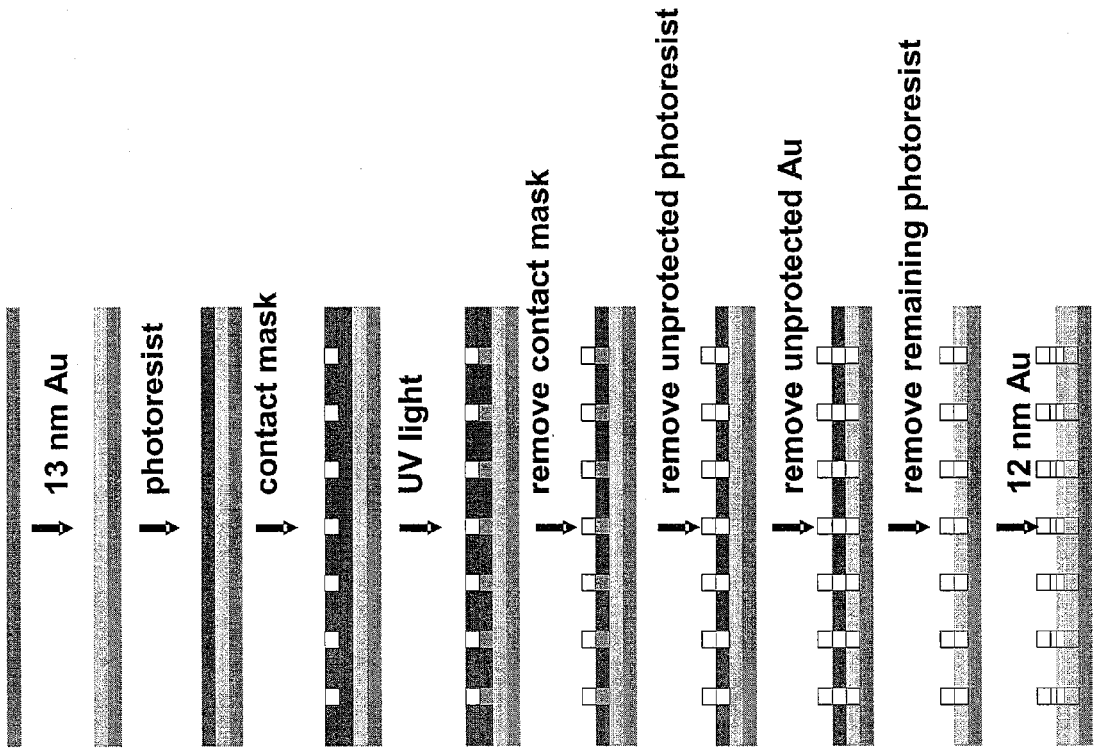
FIG. 1 is a schematic of the nanopatterning process using gold (Au) as the metallic material for the grid pattern of the marking grid.

The fiducial marker of the present invention comprises a first analytical image that overlaps a second image to correlate the two images. The first analytical image is produced by any imaging modality and is preferably produced by x-ray fluorescence microprobe (XRFM). The second image can be either another analytical image, i.e., a second analytical image or it can be a viewing image. As a preferred example of the second analytical image, Fourier transform infrared microspectroscopy (FTIRM) can be used. The correlation of the two images, in the case of the second analytical image, achieves correlation and imaging of more than one type of material in a thin sample. And, in the case of the viewing image, achieves the location of a light path, e.g., an x-ray beam of a first imaging modality with a viewing modality such as a light microscope objective which produces a viewing image of the thin sample.

The basic components of the fiducial marker are the sample substrate and the marking grid having a grid pattern coated on the surface of the substrate. The grid pattern is imageable by the first imaging modality and either a second imaging modality or a viewing modality. The imaging modality as used herein is an analytical modality, i.e., an instrument that is used to form an image of a sample, such as the thin sample, by means of the light path that enables the analyst to analyze the thin sample and different materials contained within the thin sample. Examples, include but are not limited, to x-ray fluorescence and Fourier transform infrared microspectroscopy. However, the light path of the first imaging modality is not capable of being viewed by the at least one second modality. The viewing modality as used herein is a viewing instrument that is used to view the sample, such as the thin sample, by means of, for example, the light microscope objective.

As mentioned, the present invention relates to the fiducial marker for correlating the first analytical image produced by the first imaging modality having the light path with at least one second image produced by at least one second modality. The fiducial marker comprises the sample substrate having a surface, and the marking grid having the grid pattern coated on the surface. The marking grid is composed of a metallic material that is substantially free of contaminants. The grid pattern is imageable by the first imaging modality and by the at least one second imaging modality. The ability to make the correlation between the two images enhances the analysis of a thin sample by the first imaging modality. The correlation is achieved by having the first analytical image overlap the at least one second image.

The fiducial marker of the present invention is particularly useful when the light path of the first imaging modality cannot be viewed by the at least one second modality (i.e., where the second modality is a viewing modality). Thus, the fiducial marker of the present invention is particularly useful when the at least one second image is a viewing image, the at least one second modality is a viewing modality, and the marking grid has one thickness. Preferably, the at least one second image is a visible light microscope image and the at least one second modality is a light microscope objective. Preferably, the first imaging modality is x-ray fluorescence microprobe and the light path is an x-ray beam.

Specifically, a fiducial marker of the present invention is one that is used to correlate the first analytical image produced by an x-ray beam of an x-ray fluorescence microprobe with a light microscope objective for producing a viewing image of the thin sample. The fiducial marker comprises the substrate having a surface, and the marking grid having the grid pattern coated on the surface. The marking grid has one thickness, and the grid pattern is imageable by x-ray fluorescence and by the light microscope objective. But, the x-ray beam cannot be visualized by the light microscope objective.

Another fiducial marker of the present invention is one that is used to correlate a first analytical image and at least one second analytical image produced by at least one second imaging modality. The fiducial marker comprises the sample substrate having a surface, and the marking grid having the grid pattern coated on the surface. The grid pattern has at least two pattern thicknesses and is imageable by the first imaging modality and by the at least one second imaging modality. The first and the second analytical images overlap one another to achieve the correlation and permit the thin sample to be analyzed. This is especially beneficial when the thin sample contains more than one type of material to be analyzed (e.g., organic material and trace material). Preferably, the second analytical image is Fourier transform infrared microspectroscopy.

In one method of the present invention, the second image is a viewing image produced by a viewing modality and the marking grid has one thickness. The first analytical image is produced by x-ray fluorescence microprobe having as its light path an x-ray beam, and is correlated with the viewing image to analyze the thin sample. The marking grid is patterned on a surface of a substrate and is imageable by the x-ray fluorescence microprobe. A first image grid pattern is produced using x-ray fluorescence microprobe and a viewing image grid pattern is produced by the viewing modality. The first image grid pattern and the viewing image grid pattern are co-registered, and therefore, the x-ray beam can be located and correlated with the viewing image. The x-ray beam, i.e., the light path, otherwise cannot be visualized by the light microscope objective. Thus, the correlation achieved with the fiducial marker of the present invention permits the x-ray beam to be located. Preferably, the viewing image is a light microscope image and the viewing modality is a visible light microscope objective.

In another method of the present invention, the second image is the analytical image, and it is produced by a second imaging modality. In this case, the marking grid has at least two pattern thicknesses. The marking grid is patterned on a surface of a substrate and is imageable by the first imaging modality, e.g., the x-ray fluorescence microprobe, and by the at least one second imaging modality. A first image grid pattern is produced using x-ray fluorescence microprobe and at least one second image grid pattern is produced by the at least one second imaging modality. The first image grid pattern and the at least one second image grid pattern are co-registered, and therefore, the x-ray fluorescent image (i.e., the first image grid pattern) can be located and correlated with the second image and the viewing image. The x-ray image otherwise is not easily correlated with the at least one second image. Preferably, the second analytical image is produced by Fourier transform infrared microspectroscopy as the second imaging modality.

As noted above, x-ray fluorescence microprobe has the x-ray beam as its light path. Thus, the fiducial marker can be used to correlate the first analytical image produced by the first imaging modality with the second analytical image produced by a second imaging modality, e.g., Fourier transfer infrared microspectroscopy. Consequently, the fiducial marker of the present invention using the two images produced by the two imaging modalities permits more than one aspect of the thin sample to be analyzed. The two analytical images can be correlated precisely, with a spatial resolution of less than one pixel (i.e., 2 to 3 microns). By using more than one imaging modality to analyze the same sample using the fiducial marker of the present invention, a more complete picture of many disease states and exposure to environmental contaminants can be achieved by directly correlating the organic and trace metal ion distribution in the thin sample. Preferably, the thin sample is a biological sample containing organic matter and the trace metal zinc.

The present invention also includes a method of viewing an analytical image of a thin sample using x-ray fluorescence microprobe having an x-ray beam that cannot be visualized by a light microscope objective. The steps of this method are basically the same as the steps of the other methods except that they are applied specifically to the x-ray fluorescence microprobe and the light microscope objective. A marking grid is patterned on the surface of the substrate. The marking grid is imageable by the x-ray fluorescence microprobe and by the light microscope objective. An analytical image grid pattern is produced with the x-ray fluorescence microprobe and a viewing image grid pattern is produced with the light microscope objective. The two image grid patterns are co-registered to correlate the x-ray beam of the x-ray fluorescence microprobe with the viewing image (e.g., the light microscope objective).

The marker and the method of using it can further include co-registering at least one second analytical image grid pattern with the viewing image grid pattern and the first analytical image grid pattern. In this case there is an at least one second analytical image which with the at least one second analytical image grid pattern are produced by the at least one second imaging modality. Thus, a first of the at least one second image is a viewing image produced by a viewing modality, a second of the at least one second image is an analytical image produced by an at least one second imaging modality. More specifically, the first of the at least one second image is a viewing image produced by a light microscope objective, the second of the at least one second image is an analytical image produced by Fourier transfer infrared microspectroscopy. In any of these scenarios the marking grid has at least two pattern thicknesses.

The marking grid has a grid pattern that permits the calibration of images generated by the first imaging modality and the at least one second image. The grid pattern can be any pattern; but, a particular benefit is achieved using an array of crosshairs, e.g., a "+" shapes. Other variations of the grid pattern, besides the crossbar pattern, include but are not limited to, dots, posts, circles, and chevrons. Preferably, the grid pattern is an array of crosshairs that forms squares wherein each side of the square is separated by a bar (i.e., part of the crosshair). The dimensions of the squares and the width of the bars between each side of the squares is dependent on the particular application of the marking grid. For example, the desirable width of the bar can relate to the size of the x-ray beam, infrared beam, or any other light path. Thus, the size of the bar can be in a range of about 50 nanometers to about 20 microns. The space between the bars, i.e., the width of the square or the pitch, depends on the size of the sample to be analyzed. The width of the squares is represented by the pitch (i.e., the distance between two adjacent bars.) At least one cross-hair needs to fall on the area of the sample. Considering a typical sample is about 0.1 to about 5.0 millimeters in area, each side of the square is preferably, about 50 microns to about 250 microns. Preferably, the grid pattern is an array of about 190 micron wide squares with a center-to-center spacing of about 200 microns from square to square. Each square is separated by a gap of about 10 microns.

The marking grid is composed of a metallic material that is substantially free of contaminants that would interfere with the desired measurement of ppm (parts per million) concentrations in the thin sample. Thus, the marking grid can be composed of a solid pure (e.g., 99.9999% purity) reflective metal. As used herein, a material that is substantially free of contaminants contains less than 0.0001% contaminants. The metal of the marking grid is not a metal salt.

Preferably, the marking grid is a reflective solid metal. It is desirable for the metal of the marking grid to not interfere with the first imaging modality, or either the second imaging modality or viewing modality depending on which one or more is present. Many metals can be used to make the marking grid depending on the thin sample, and the imaging and viewing modalities or the imaging modalities that are used with the fiducial marker of the present invention. Thus, the metallic material selected for the marking grid depends on whether the material will interfere with the desired material being measured in the thin sample and whether the material will interfere with the analytical instrumentation (i.e., the imaging modalities or imaging and viewing modalities) used for the measurement. One of ordinary skill in the art would be able to select a desired metal. Most metals are infrared-reflective and give an x-ray fluorescence signal. While any solid reflective metal can be used, preferably, the marking grid is a solid reflective metal of gold, titanium, aluminum or chromium depending on the analysis. More preferably, the solid metal of the grid pattern is either gold or chromium depending on the analysis. More preferably still, the solid metal is gold when at least two imaging modalities are used and the solid metal is chromium or gold when at least one imaging modality is used and a viewing modality is used.

In one example, the metallic material is preferably chromium (Cr) when the desired measured material in the thin sample is zinc, the first analytical image is produced by x-ray fluorescence microprobe having the x-ray beam as the light path, and the second image is a viewing image produced by a viewing modality. The fiducial marker is used to correlate a first analytical image having a light path with at least one second image produced by at least one second modality to analyze a thin sample containing a material to be measured. The light path cannot be visualized by the at least one second modality. Preferably, the viewing image is a visible light microscope image produced by a conventional light microscope objective. The pure Cr is in the metallic (elemental) form of for example, a chip, shot or wire, available commercially from ESPI, Ashland, Oreg., In another example, gold (Au) shot preferably having a purity of at least 99.9999% is available commercially from ESPI, Ashland, Oreg., is used as the reflective solid metal to produce the grid pattern on the substrate when the analysis uses x-ray fluorescence microspectroscopy as the first imaging modality and Fourier transform infrared microprobe as the second imaging modality. Specifically, the metal of the marking grid does not have an interfering fluorescence emission line with the thin sample. In other words, the metallic material does not interfere with the first imaging modality or the second imaging modality.

The marking grid has either a single thickness or a plurality of thicknesses depending on the analysis. On one hand, when there is a viewing modality involved in the analysis, the marking grid has one thickness. And on the other hand, when there are at least two imaging modalities, there are at least two thicknesses for the marking grid. Preferably, one of the pattern thicknesses of the grid pattern generates a first reflectivity as a function of the second imaging modality, for example, Fourier transform infrared microspectroscopy, and the other pattern thicknesses generates a second reflectivity as a function of the at least one second imaging modality. It is further preferable for one of the pattern thicknesses of the grid pattern to generate a reflectivity sufficient to differentiate the one thickness from the other thickness(es) as a function of the second imaging modality. Further preferable still, when the at least one second imaging modality is an analytical image produced by Fourier transform infrared microspectroscopy, one of the at least two pattern thicknesses has a reflectivity of about 70% to about 90% in an infrared region, and the other of the at least two pattern thicknesses has a reflectivity of about 100% in the infrared region. In addition, when the metallic material is gold, the one of the at least two pattern thicknesses has about 75% to about 85% reflectivity in the infrared region, and the other of the at least two pattern thicknesses has about 100% reflectivity in the infrared region.

In the case of the second image that is a viewing image, the marking grid has one thickness. When there is one imaging modality and one viewing modality, the grid pattern has a single pattern thickness. The single layer permits the light path of the first imaging modality to be located by correlating the first analytical image with the second viewing image produced by the viewing modality. The minimum thickness of the single layer depends on the sensitivity of the imaging modality. Therefore, the thickness of the single layer is about 1 nanometer to about 300 nm in thickness. Preferably, the coating formed as a single layer by vacuum evaporation can be about 2 nm to about 100 nm. The upper limit of this range is flexible as it is possible to tune the monochromator to the leading edge of the absorption peak to minimize the fluorescence. A first image grid pattern is produced of the biological sample as a first sample image. The marking grid is a metal that does not interfere with the biological sample.

In the case of the second image that is an analytical image produced by at least one second imaging modality, the fiducial marker has a marking grid of at least two pattern thicknesses. Preferably, the marking grid is composed of solid pure gold (Au). When there are at least two imaging modalities, the marking grid has at least two different pattern thicknesses that form dual layers of the grid pattern. The two thicknesses are used to correlate the first analytical image with the second analytical image. As used herein, the term "pattern thickness" is intended to mean the height of the grid pattern from the surface of the sample substrate. In general, with the two different pattern thicknesses, the absolute thickness of the square and the bar of the grid pattern is not as important as the difference between the thickness of the square and the bar. However, where one of the two imaging modalities is infrared, the desirable thickness falls within a range based on the metal used for the marking grid. The bars are a thickness to yield about 70% to about 90% infrared reflectivity (about 12 to 15 nm for gold) and the squares should be a thickness to yield about 100 percent infrared reflectivity (greater than about 20 nm for gold).

As an example, the one pattern thickness of the grid pattern is a fraction of about one-half or less than the other of the at least two pattern thicknesses when the first analytical image is produced by x-ray fluorescence microprobe, the at least one second image is an analytical image produced by Fourier transfer infrared microspectroscopy, and the metal of the marking grid is gold. Further, in the case of this example, it is preferable that one pattern thickness (i.e., the bars) is about 8 to 12 nm, and the other pattern thickness (i.e., the squares) is greater than about 20 nm.

The thin sample is deposited on the marking grid for analysis and as a result of analytical instrumentation (i.e., the imaging modalities) produces the first analytical image of the thin sample, a second analytical image or a viewing image of the thin sample. In each image, the thin sample appears in the midst of a corresponding first image grid pattern and either a viewing image grid pattern or at least one second image grid pattern. The thin sample can be any type of sample matter prepared as a thin section for analysis. The typical sample is about 0.1 to about 5.0 millimeters in area. The thin sample can include but is not limited to biological, plant, rock, mineral, polymeric, or tissue.

Preferably, the thin sample is biological such as for example, protein (e.g., paraffin-embedded metalloprotein crystals (i.e., myoglobin) snap-frozen brain specimen, and hair. The biological sample is immobilized such that it can be cut into thin sections. Sample thickness should be as thin as possible, about 100 nm to 0.5 mm. The limit to the degree of "thinness" attainable is based on the diameter of the sample, which is about 1 mm to about 2 inches (i.e., 5.08 cm).

More preferably, the thin biological sample contains organic matter and a trace metal. The trace metals can be for example, potassium, calcium, manganese, cobalt, nickel, molybdenum, mercury, lead, iron, copper and zinc. Preferably, the trace metal is zinc, potassium, calcium, iron or copper. The trace metal is preferably imageable by x-ray fluorescence microprobe. While, the organic matter is preferably imageable by the at least one second imaging modality. More preferably, the second imaging modality is Fourier transform infrared microspectroscopy. The metal of the marking grid is preferably one that does not interfere with the trace metal in the biological sample.

The biological sample is imaged by the first imaging modality to produce a first analytical image of the biological sample with a first image grid pattern. Using the at least one second imaging modality, the biological sample is imaged to produce at least one second analytical image of the biological sample with at least one second image grid pattern. Thus, a means is provided for analyzing both trace metals and organic matter or other materials without the need for extrinsic stains or labels. The absorbance of a biological sample to be analyzed with the imaging modality can interfere with the reflectivity image. As a result, therefore, the entire grid pattern may not be visible. However, as long as one cross-bar (or cross-hair) of the grid pattern is visible, image overlap can be achieved.

The sample substrate consists of a material that is a low trace element material, and is thin. Typically, the thickness of the sample substrate is greater than about 100 nm and less than about 2 mm thin. The sample substrate supports the metallic material of the marking grid. The sample substrate can be transparent or opaque. If the sample substrate is opaque top (front) illumination can be provided. Examples of materials that may be suitable as the substrate, include but are not limited to, glass (also referred to as silica or quartz), silicon, silicon nitride, mylar, kapton, polyethylene, and polypropylene; as well as polymers such as Ultralene®, commercially available from SPEX CertiPrep (Metuchen Scientific), Metuchen, N.J., 08840. Preferably, the glass substrate is a pure glass in the form of fused silica. The form of the substrate can be a slide, and the glass slide can be any shape. However, preferably, the low trace element glass slide is a disc. Specifically, the low trace element glass slide can be a low trace element Suprasil 2 fused silica disc (1.5" (inch) diameter×0.063" (inch) thickness), commercially available from Heraeus Optics, Buford, Ga. The diameter of the grid depends on the mask used to make the grid pattern. However, a thinner substrate is preferred because it reduces the scattering of x-ray and thus, has a higher sensitivity to trace metals. Preferably, therefore, the thickness of the substrate is greater than about 100 nm and less than about 0.5 mm thin.

To produce the grid pattern having two thicknesses on the sample substrate with gold as the metal of the marking grid, a dual deposition process is used. A layer of Au between 10 to 20 nm is first evaporated onto the sample substrate, e.g., the fused silica disk. Similarly, for Cr or other metallic materials, high purity Cr chips are placed in a small tungsten wire basket that is heated to greater than about 2,000 C to evaporate the Cr in a vacuum evaporator. The thickness of the Au layer is measured by a quartz crystal monitor (error is about ±2 nm). A photoresist layer, for example, Shipley 1881 positive photoresist available commercially from 455 Forest St, Marlborough, Mass., 01752, is spin coated over the evaporated layer of Au.

After applying the photoresist layer, a 4" chrome-on-glass contact mask (with clear/open lines to form the bars and solid spaces to form the square/pitch), available from Advanced Reproduction Corp., North Andover, Mass. 01845, is placed on the disk, and exposed to about 350-450 nm UV light, using an Oriel 27240 exposer with 350 watt Hg lamp, for about 45 seconds to activate the photoresist layer. The exposed photoresist layer is removed by first submerging the disk for about 30 seconds in about a 1:1 ratio of MF-312 developer and water followed by a water rinse. The portion of the Au layer unprotected by the photoresist layer is removed with about a 3:1 HCl:HNO$_3$ solution. The remaining photoresist is removed with acetone leaving only the major part of the pattern of the Au layer with a thickness of between 10 to 20 nm. A second layer of Au is evaporated over the entire disk at a thickness of between 10 and 20 nm, making the final grid thickness between 10 and 20 nm in portions that were exposed (the minor portion) and the remainder of the disc is between 20 and 40 nm in portions that were unexposed (the major portion). A schematic showing the nanopatterning process can be seen in FIG. 1. When making a single layer marking grid a similar process is used with a mask that has sold lines to form the bars and clear/open spaces to form the square/pitch. In addition, it is within the skill of the art of etching and deposition processes to form marking grids with greater than two thicknesses based on the foregoing.

The viewing image grid pattern and the analytical image grid pattern are used as fiducial markers to spatially overlap the viewing image and the analytical image. Results show that the images can be correlated precisely, with a spatial resolution of less than one pixel, i.e. 2-3 microns. The fiducial marker of the present invention is useful in analyzing samples of paraffin-embedded metalloprotein crystals, Alzheimer's disease, and hair composition.

EXAMPLES

1. Single Deposition Process of the Present Invention (5 µm)

A. Chromium Deposition Sequence

To produce the grid pattern on the substrate with chromium as the metal of the marking grid, a single deposition process is used. A 2 inch diameter high-purity quartz disc (quartz wafer), the substrate, is washed in an aqueous solution containing "Micro" laboratory cleaner (International Products Corp., Burlington, N.J., 08016) in an ultrasonic cleaner to remove organic films from the substrate. The substrate is rinsed with deionized water and then placed in boiling isopropanol to ensure that any residual water goes into solution and is removed from the substrate. To remove any adsorbed water monolayers, the substrate is baked for 30 min. at 120° C. Immediately after baking, the substrate is placed in a vacuum evaporator very close to a crystal thickness monitor and the system is pumped to achieve a vacuum better than $10^{-6}$ torr.

A small tungsten wire basket is filled with chromium pellets with a purity of better than 99.9999% and is used as the evaporation source. After the vacuum is achieved, the tungsten basket is then resistance-heated to melt the chromium and deposit a 5 nanometer thick chromium film at a rate of 0.1 nanometer/second on the substrate (quartz wafer).

B. UV Lithograph Exposure Steps

The chromium-coated quartz substrate is placed in a photoresist spinner manufactured by Headway Research, Model No. EC101D. A thin HMDS (hexamethyldisilizane) layer is created on the substrate by spraying a few milliliters of HMDS on the substrate and then spinning the substrate at 3,000 RPM for 20 sec. with the photoresist spinner. The thin HMDS layer increases the adherence of Shipley 1811 photoresist (Shipley Company LLC, 455 Forest St, Marlborough, Mass., 01752). Add a few milliliters of Shipley 1811 photoresist to the substrate to cover the surface and spin at 4,000 RPM for 30 sec. to spread the resist as an even layer over the substrate. Bake the resist-coated substrate for 2 min. at 115° C. on a hot plate to evaporate off solvents in the photoresist and form an adherent photoresist layer that is sensitive to UV radiation.

Place the resist-coated substrate in close contact with a quartz mask (solid lines and clear spaces), commercially available from Advance Reproductions, North Andover, Mass., containing a chrome representation of the grid pattern to be transferred to the photoresist. In this example, the grid pattern consists of a grid pattern with a bar width of 15 microns and a center-to-center spacing of 200 microns from bar to bar. Expose the resist-coated substrate for 12 sec. at 12 milliwatts/cm$^2$ with a broad spectrum mercury lamp that produces UV radiation (with a line spectrum ranging from 190 to 400 nanometers of UV radiation) in a Karl Suss Microtec MJB-3 contact mask aligner with a high pressure mercury lamp, USH-3500DS made by Ushio, Inc. Japan. Develop for 25 sec. using Shipley MF 312 developer diluted 1:1 with water in an amount of about 250 ml. Photoresist regions that are covered by the chrome pattern during exposure are not exposed to UV radiation and remain on top of the chromium film. Photoresist regions that are exposed to UV radiation become soluble in the developer and are dissolved by the developer. These exposed regions of the chromium film are etched away in the "Chromium Etching Steps" described below. Wash in water and bake the developed resist-coated disc for 2 min. at 120° C. on a hotplate to dry. At the conclusion of these steps, the chromium film is covered by grid pattern of photoresist that has a bar width of 15 microns and a center-to-center spacing of 200 microns. Chromium regions protected by the photoresist squares are not etched in the following steps.

C. Chromium Etching Steps

Figure 11:
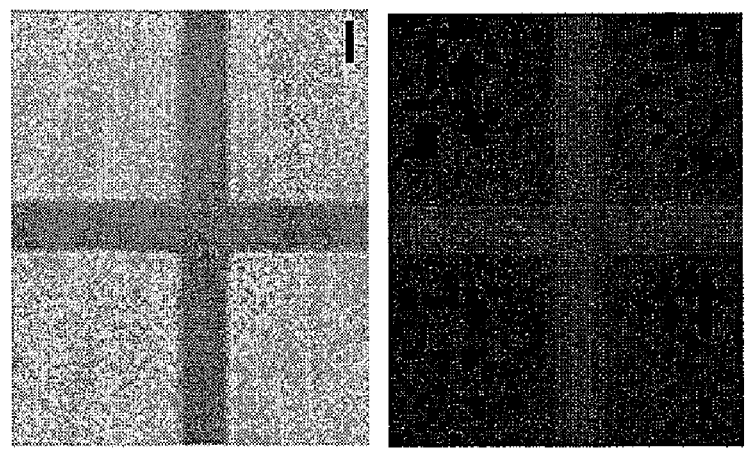
FIG. 11 (top) illustrates a visible light illumination of a single layer chromium grid pattern using a light microscope (white light)
Figure 10:
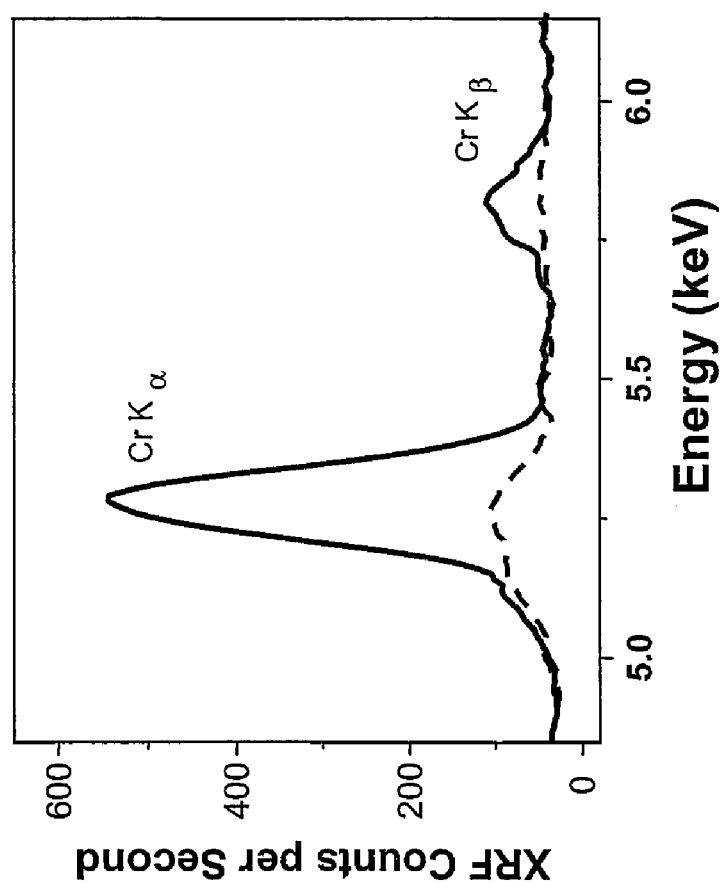
FIG. 10 displays the integrated chromium fluorescence intensity of the single layer Cr grid (solid line) and the integrated chromium fluorescence intensity of the remainder of the sample substrate (dashed line) as depicted by a plot of XRF counts per second versus energy (keV).

Etch the chromium film a volume of 200 milliliters of chromium mask etchant supplied by Transene Company, Danvers, Mass., in an amount sufficient to submerse the substrate for 5 seconds at ambient temperature to etch a rectangular grid pattern. After etching is complete, use acetone to dissolve the photoresist. At the conclusion of this step, the chromium film on the substrate is patterned to form a single layer grid with a bar width of 15 microns and a center-to-center distance of 200 microns. Each bar is separated by a 185 micron boundary where the chromium has been etched away leaving the underlying quartz substrate visible. The single layer chromium grid pattern is 5 nanometers in thickness. The resultant single layer Cr marking grid is illustrated in FIG. 10, FIG. 11 (top) and FIG. 11 (bottom). For XRFM, in FIG. 10, Cr fluorescence was observed from the grid (solid line), whereas negligible Cr fluorescence was observed from the surrounding area (dashed line). Similar to the FTIRM results and the XRFM results for the dual layer marking grid, the sharpness of the bar edge was 2-3 µm, as can be seen in the Cr XRFM (x-ray fluorescence) image of the single layer marking grid (FIG. 11 (bottom)).

2. Dual Deposition Process of the Present Invention (9 and 14 nm)

A. First Gold Deposition Sequence

To produce the grid pattern on the substrate with gold as the metal of the marking grid, a dual deposition process is used. A 2 inch diameter high-purity quartz disc (quartz wafer), the substrate, is washed in an aqueous solution containing "Micro" laboratory cleaner (International Products Corp., Burlington, N.J., 08016) in an ultrasonic cleaner to remove organic films from the substrate. The substrate is rinsed with deionized water and then placed in boiling isopropanol to ensure that any residual water goes into solution and is removed from the substrate. To remove any adsorbed water monolayers, the substrate is baked for 30 min. at 120° C. Immediately after baking, the substrate is placed in a vacuum evaporator very close to a crystal thickness monitor and the system is pumped to achieve a vacuum better than $10^{-6}$ torr.

A small tungsten wire basket is filled with gold pellets with a purity of better than 99.9999% and is used as the evaporation source. After the vacuum is achieved, the tungsten basket is then resistance-heated to melt the gold and deposit a 5 nanometer thick gold film at a rate of 0.1 nanometer/second on the substrate (quartz wafer).

B. UV Lithograph Exposure Steps

The gold-coated quartz substrate is placed on a photoresist spinner Headway Research, Model No. EC101D. A thin HMDS (hexamethyldisilizane) layer is created on the substrate by spraying a few milliliters of HMDS on the substrate and then spinning the substrate at 3,000 RPM for 20 sec. on the photoresist spinner. The thin HMDS layer increases the adherence of Shipley 1811 photoresist (Shipley Company LLC, 455 Forest St, Marlborough, Mass., 01752). Add a few milliliters of Shipley 1811 photoresist to the substrate to cover the surface and spin at 4,000 RPM for 30 sec. to spread the resist as an even layer over the substrate. Bake the resist-coated substrate for 2 min. at 115° C. on a hot plate to evaporate off solvents in the photoresist and form an adherent photoresist layer that is sensitive to UV radiation.

Place the resist-coated substrate in close contact with a quartz mask (clear lines and solid spaces), commercially available from Advance Reproductions, North Andover, Mass., containing a chrome representation of the grid pattern to be transferred to the photoresist. In this example, the grid pattern consists of an array of 185 micron wide squares with a center-to-center spacing of 200 microns from square to square. Expose the resist-coated substrate for 12 sec. at 12 milliwatts/cm$^2$ with a broad spectrum mercury lamp that produces UV radiation (with a line spectrum ranging from 190 to 400 nanometers of UV radiation) in a Karl Suss Microtec MJB-3 contact mask aligner with a high pressure mercury lamp, USH-3500DS made by Ushio, Inc. Japan. Develop for 25 sec. using Shipley MF 312 developer diluted 1:1 with water in an amount of about 250 ml. Photoresist regions that are covered by the chrome pattern during exposure are not exposed to UV radiation and remain on top of the gold film. Photoresist regions that are exposed to UV radiation become soluble in the developer and are dissolved by the developer. These exposed regions of the gold film are etched away in the "Gold Etching Steps" described below. Wash in water and bake the developed resist-coated disc for 2 min. at 120° C. on a hotplate to dry. At the conclusion of these steps, the gold film is covered by an array of photoresist squares that measure 185 microns on a side separated by a gap of 15 microns between each square. Gold regions protected by the photoresist squares are not etched in the following steps.

C. Gold Etching Steps

Etch gold film in 3 parts HCL acid+1 part HNO$_3$ acid in a volume of 100 milliliters, an amount sufficient to submerse the substrate for 5 seconds at ambient temperature to form a rectangular grid pattern. After etching is complete, use acetone to dissolve the photoresist. At the conclusion of this step, the gold film on the substrate is patterned to form an array of gold squares, 185 microns on a side. Each square is separated by a 15 micron boundary where the gold has been etched away leaving the underlying quartz substrate visible. Each square is 5 nanometers in thickness.

D. Second Gold Deposition Sequence

Deposit an additional 9 nanometer gold film over the entire substrate by placing the substrate in a vacuum evaporator very close to a crystal thickness monitor and pumping the system to achieve a vacuum better than $10^{-6}$ torr. Fill a small tungsten wire basket with gold pellets with a purity of better than 99.9999% as the evaporation source. After the vacuum is achieved, the tungsten basket is resistance-heated to melt the gold and a 9 nanometer thick gold film is deposited at a rate of 0.1 nanometer/second on the substrate (quartz wafer). At the conclusion of this step, the gold film on the quartz wafer again covers the entire wafer. The thickness over the gold squares is the sum of the two independent depositions: 5+9 nanometers=14 nanometers. The thickness of the gold in the boundary between the squares is 9 nanometers, since it was directly deposited on the quartz substrate.

3. Characterization of Marking Grid of the Present Invention (12 and 25 nm)

A. Dual Deposition Process of the Present Invention

The following steps are followed to produce a grid pattern on the surface of the sample substrate, where the major and minor parts of the grid contain 25 and 12 nm Au, respectively. To produce the grid pattern on the substrate with gold as the metal of the marking grid, a dual deposition process is used. A 2 inch diameter high-purity fused silica disc, the substrate, is washed in an aqueous solution containing "Micro" laboratory cleaner (International Products Corp., Burlington, N.J., 08016) in an ultrasonic cleaner to remove organic films from the substrate. The substrate is rinsed with deionized water and then placed in boiling isopropanol to ensure that any residual water goes into solution and is removed from the substrate. To remove any adsorbed water monolayers, the substrate is baked for 30 min. at 120° C. Immediately after baking, the substrate is placed in a vacuum evaporator very close to a crystal thickness monitor and the system is pumped to achieve a vacuum better than $10^{-6}$ torr.

A small tungsten wire basket is filled with gold pellets with a purity of better than 99.9999% is used as the evaporation source. After the vacuum is achieved, the tungsten basket is then resistance-heated to melt the gold and deposit a 13 nanometer thick gold film at a rate of 0.1 nanometer/second on the substrate (fused silica disc).

The thickness of the gold layer is measured by a quartz crystal monitor (error is about ±2 nm). A photoresist layer of Shipley 1881 positive photoresist, available commercially from Shipley Company LLC, 455 Forest St, Marlborough, Mass., 01752, is spin coated over the evaporated layer of Au. The gold-coated quartz substrate is placed on a photoresist spinner. A thin HMDS (hexamethyldisilizane) layer is sprayed on the substrate and then the substrate is spun at 3,000 RPM for 20 sec. on a photoresist spinner. The thin HMDS layer increases the adherence of Shipley 1811 photoresist. Add a few milliliters of Shipley 1811 photoresist to the substrate to cover the substrate, and spin at 4,000 RPM for 30 sec. to spread the resist as an even layer over the substrate. Most of the resist is flung off during the spinning process to leave an even film that is a fraction of a micron in thickness after baking. Bake the resist-coated substrate for 2 min. at 115° C. on a hot plate to evaporate off solvents in the photoresist and form an adherent photoresist layer that is sensitive to UV radiation.

After applying the photoresist layer, a 4" chrome-on-glass contact mask, available from Advanced Reproduction Corp., North Andover, Mass. is placed on the disk, and exposed to about 350-450 nm UV light, using an Oriel 27240 exposer with 350 watt Hg lamp, for about 45 sec. to activate the photoresist layer. The exposed photoresist layer is removed by first submerging the disk for about 30 seconds in a 1:1 ratio of MF-312 developer and water and then a water rinse. The portion of the Au layer that was not protected by the photoresist layer is removed with a 3:1 $HCl:HNO_3$ solution (100 ml). The remaining photoresist is removed with acetone leaving only the major part of the pattern of the gold layer with a thickness of about 13 nm. A second layer of gold is evaporated over the entire disk at a thickness of 12 nm, making the final grid thickness 12 nm in portions that were exposed and the remainder of the disk is 25 nm in portions that were unexposed. A schematic showing the dual deposition process can be seen in FIG. 1.

B. Marking Grid Characterization.

Figure 3:
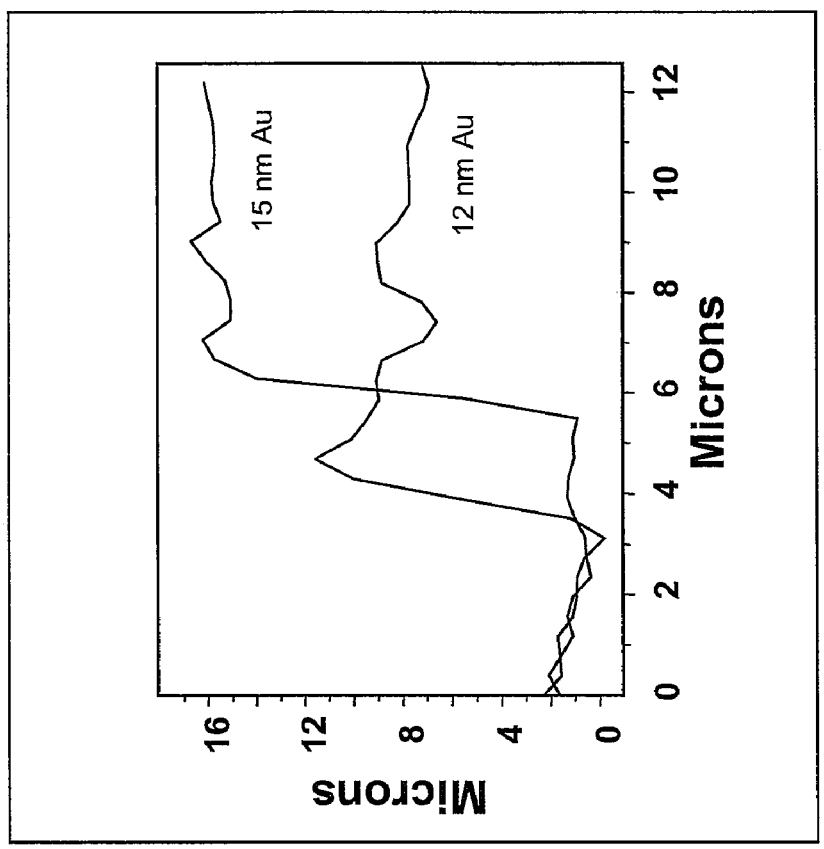
FIG. 3 displays the atomic force microscopy results of a line scan from clean glass substrate to a grid bar which results in a step up of about 12 nm, where the sharpness of the step is <1 μm; and a line scan from the grid bar to an open area results in a step jump of about 15 nm, where the sharpness of the step edge is <1 μm.
Figure 2:
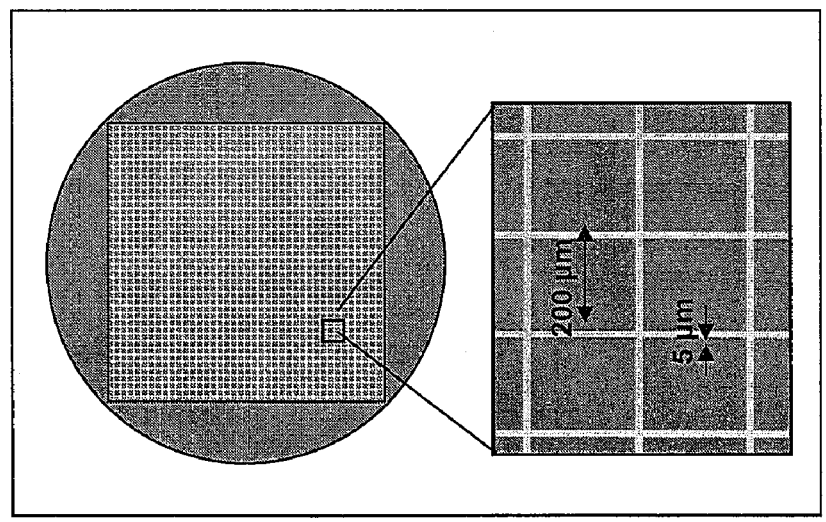
FIG. 2 illustrates a gold grid pattern on a glass substrate with an exploded view of a section of the grid pattern showing a width of the gold bar of 15 μm and a pitch (distance between bars) of 200 μm.

FIG. 2 illustrates a schematic of the gold grid pattern on the glass substrate. From light microscopy, it can be seen that the width of the gold bar is 15 µm and the pitch (distance between bars) is 200 µm. In order to assess the thickness of the gold pattern, atomic force microscopy was performed (FIG. 3). A line scan from clean glass to the grid bar showed that the step up was approximately 12 nm, where the sharpness of the step was <1 µm. A line scan from the grid bar to the open area showed that the step jump was approximately 15 nm, where the sharpness of the step edge was <1 µm. Thus, the thickness of the gold bar was confirmed to be 12 nm and the gold on the remainder of the disk was approximately 27 nm thick.

Figure 6:
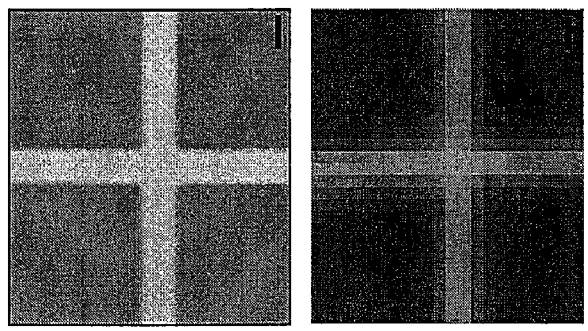
FIG. 6 (top) illustrates a visible light illumination of a gold grid pattern using a light microscope (white light), and FIG. 6 (bottom) illustrates an IR reflection image from 3800-4000 $cm^{-1}$ of the sample substrate shown in FIG. 6 (top), having a grid pattern thereon where the sharpness of the edge is 2-3 μm. Scale bar is 15 μm. in both FIG. 6 (top) and FIG. 6 (bottom).
Figure 5:
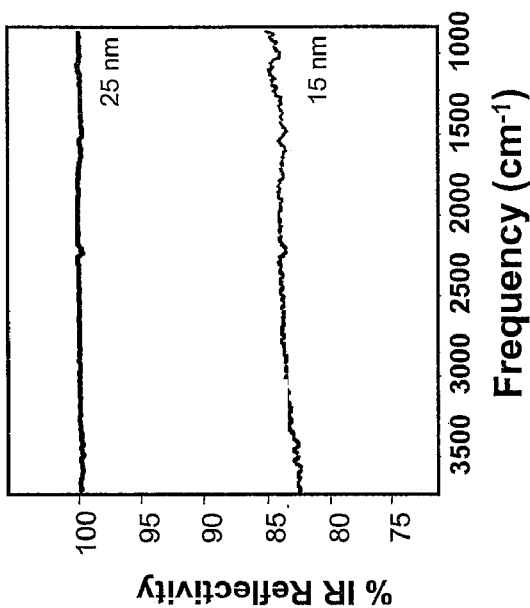
FIG. 5 displays the Fourier transform infrared spectra for 25 and 15 nm gold as indicated by a plot of % IR reflectivity versus frequency ($cm^{-1}$).
Figure 4:
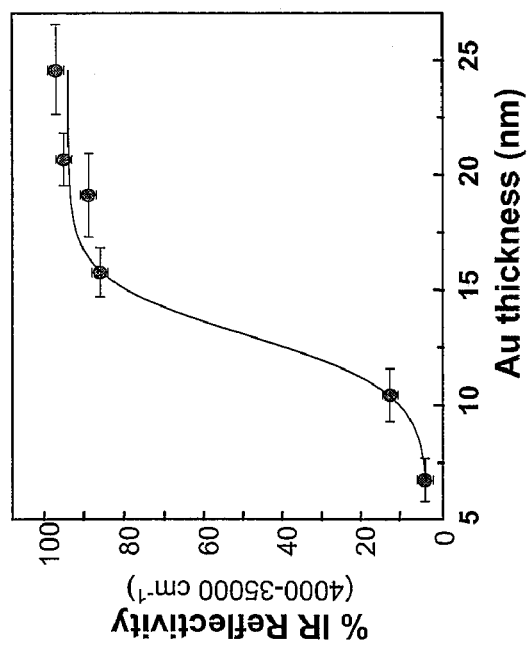
FIG. 4 shows the relationship between gold reflectivity and thickness as measured by a plot of % IR reflectivity (4000-3500 $cm^{-1}$) versus thickness of gold measured in nanometers.

The relationship between gold reflectivity and thickness can be seen in FIG. 4. Between 10 and 20 nm of Au, there is a sharp increase in reflectivity from about 10% to about 90%. Thus, the Au thickness for the grid pattern was chosen to be 12-15 nm, to provide high enough reflectivity to collect FTIR spectra, but low enough reflectivity to differentiate the thick (25 nm, 100% reflectivity) from the thinner Au. The FTIR spectra for 25 and 15 nm gold are shown in FIG. 5. As can be seen in FIG. 6, the Au reflectivity is flat over the spectral range from 4000-1000 $cm^{-1}$. An IR reflection image from 3800-4000 $cm^{-1}$ of the patterned substrate shows that the bars of the grid are clearly visible due to the reduced IR reflectivity, where the sharpness of the edge is 2-3 µm.

Figure 9:
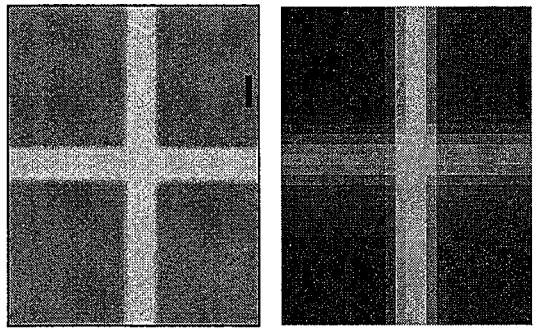
FIG. 9 (top) illustrates a visible light illumination of a gold grid pattern using a light microscope (white light)
Figure 8:
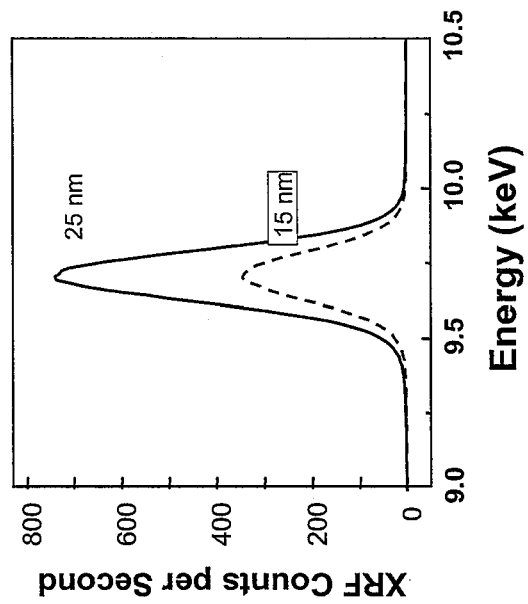
FIG. 8 in part B displays the integrated gold fluorescence intensity of the grid (solid line) and the integrated gold fluorescence intensity of the remainder of the sample substrate (dashed line) as depicted by a plot of XRF counts per second versus energy (keV).
Figure 7:
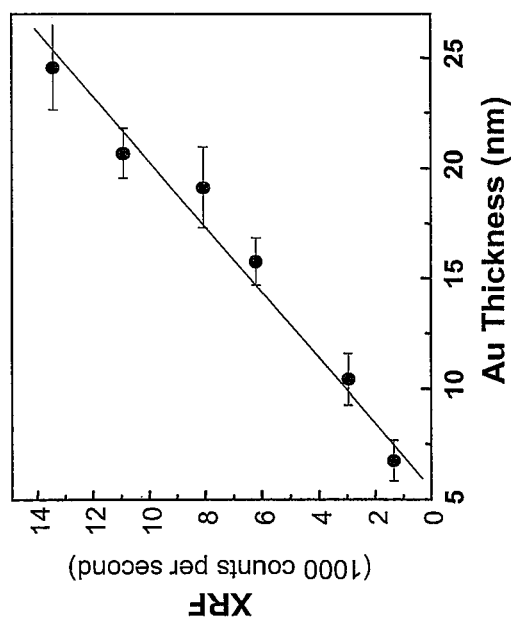
FIG. 7 shows the relationship between gold reflectivity and thickness as measured by a plot of the intensity of the fluorescence signal for gold, XRF (1000 counts per second) versus thickness of gold measured in nanometers.

For XRFM, the intensity of the Au fluorescence signal was proportional to the thickness of the Au (FIG. 7). The thickness of the grid pattern was 15 nm, which was approximately half the thickness of the remainder of the substrate (25 nm). The integrated Au fluorescence intensity of the grid (340 counts) was also approximately half of the integrated intensity from the remainder of the substrate (750 counts) (FIG. 8). Similar to the FTIRM results in FIG. 3C, the sharpness of the bar edge was 2-3 µm, as can be seen in the Au XRFM image of the grid (FIG. 9). These findings showed that both the IR and x-ray microscopes are sensitive to the Au pattern on the substrate.

4. Correlation of Metal and Organic Composition

In order to test the ability to superimpose FTIRM and SXRF images using the grid pattern, crystals of a lyophilized metalloprotein (i.e. myoglobin) were embedded in paraffin, microtomed, and a thin section was deposited on the fiducial marker having a marking grid patterned on a substrate. The location of the protein in the paraffin was determined with FTIRM, while the location of the iron in the thin section was determined with the SXRF microprobe. Since the iron is covalently bound to the protein, the two images should "perfectly" correlate, and thus provide a measure of the precision of the technique and fiducial marker of the present invention.

Figure 13:
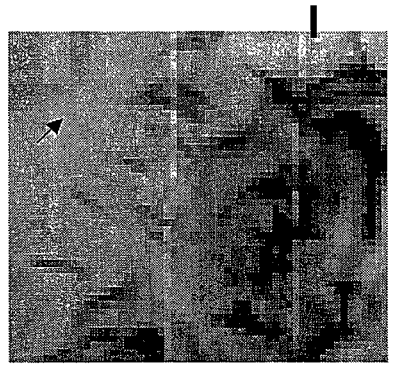
FIG. 13 shows the IR reflectivity image from 4000-3500 $cm^{-1}$ using Fourier transform infrared microspectroscopy (FTIRM). Scale bar is 20 µm.
Figure 14:
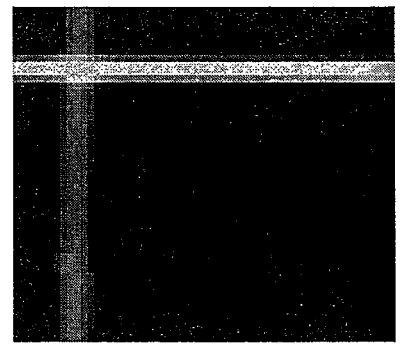
FIG. 14 shows the gold (Au) reflectivity image using synchrotron x-ray fluorescence (SXRF) microprobe. Scale bar is 20 µm.
Figure 12:
FIG. 12 shows the light microscope image of myoglobin crystals embedded in a paraffin section. Scale, bar is 20 µm.

FIG. 12 shows the light microscope image of the myoglobin crystals embedded in the paraffin section, where the location of the crystals is evident based on their red color. The Au reflectivity (FTIRM) and Au SXRF images can be seen in FIGS. 13 and 14, respectively. It is noted that the sample absorbance can interfere with the FTIRM reflectivity data so that the entire grid pattern is not visible. However, image overlap only requires one cross-bar, which is indicated by the black arrow. It should also be noted that, in some cases, the visible light image from the IR data collection is more desirable for image overlap than the IR reflectivity image. In FTIRM imaging, the visible light path for sample illumination is identical to the infrared light path for data collection, i.e. the same reflective optics are used. Thus, the visible-light and infrared images are perfectly correlated. However for SXRF imaging, this is not the case. Visible light illumination and sample magnification is performed through a glass microscope objective. The focused x-ray beam is then positioned at the focus spot (e.g. crosshair) of the light microscope image. However, if the visible light image and x-ray beam are not precisely overlapped, then the resulting XRFM images will be shifted from the light microscope images. Moreover, any motion in the x-ray beam or the visible light optics during data collection can cause a mismatch in the overlap. Since the x-ray beam is not visible during data collection, it's not obvious that this has occurred. By using an x-ray sensitive grid pattern, the position of the x-ray beam is always accurately known.

Figure 16:
FIG. 16 shows the SXRF microprobe image of iron in the same area as the FTIRM image of the Amide I band in FIG. 15. Scale bar is 20 µm.
Figure 15:
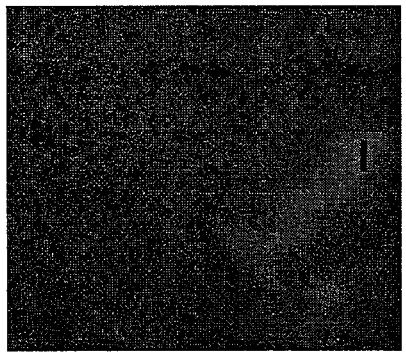
FIG. 15 shows the FTIRM image of the Amide I band (1600-1700 $cm^1$), indicative of protein. Scale bar is 20 µm.
Figure 17:
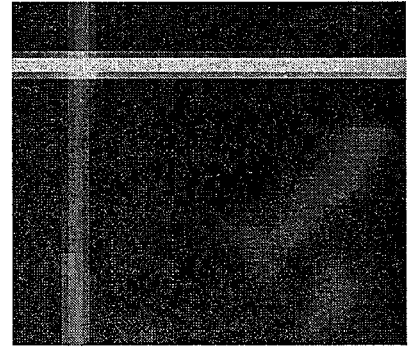
FIG. 17 shows the correlation observed between the protein and iron images in FIGS. 15 and 16, having a sub-pixel precision of about 2-3 µm. Scale bar is 20 µm.

The FTIRM image of the Amide I band (1600-1700 cm$^{-1}$), indicative of protein, can be seen in FIG. 15. Since the chemical structure of paraffin lacks any amide bonds, there is no absorbance overlap in this spectral region. The iron SXRF microprobe image of the same area can be seen in FIG. 16. The FTIRM and SXRF images were superimposed by overlapping the Au grid patterns. In this example, the FTIRM image was shifted by 16 μm to the right in the horizontal direction and 4 μm down in the vertical direction to correspond to the coordinates of the SXRF image. The outer edges of both images were cropped so that only data containing IR and SXRF information were included. As can be seen in FIG. 17, an excellent correlation was observed between the protein and iron images, where a sub-pixel precision of 2-3 μm was found.

The invention claimed is:

1. Method of correlating a first analytical image produced by x-ray fluorescence microprobe and having an x-ray beam with a viewing image produced by a viewing modality for analyzing a thin sample comprising the steps of
    a) patterning a marking grid on a surface of a sample substrate, where said marking grid is imageable by the x-ray fluorescence microprobe and has one thickness;
    b) producing a first image grid pattern by the x-ray fluorescence microprobe and a viewing image grid pattern by the viewing modality; and
    c) co-registering the first image grid pattern and the viewing image grid pattern.

2. The method of claim 1 wherein the viewing image is a visible light microscope image and wherein the viewing modality is a light microscope objective.

3. The method of claim 1 wherein the thin sample is selected from the group consisting of biological, plant, rock, mineral, polymeric, and tissue.

4. The method of claim 1 wherein the thin sample is biological.

5. The method of claim 4 further comprising the step of depositing the biological sample on the marking grid.

6. The method of claim 4 wherein the step of producing the first image grid pattern further comprises producing a first analytical image of the biological sample.

7. The method of claim 4 wherein the step of producing the viewing image grid pattern further comprises producing a viewing image of the biological sample.

8. The method of claim 4 wherein the marking grid is a metal that does not interfere with the biological sample.

9. Method of correlating a viewing image produced by a viewing modality, a first analytical image produced by x-ray fluorescence microprobe having an x-ray beam and at least one second analytical image produced by at least one second imaging modality for analyzing a thin sample, wherein said x-ray beam cannot be viewed in the viewing image, comprising the steps of
    a) patterning a marking grid on a surface of a sample substrate, where said marking grid has at least two pattern thicknesses and is imageable by the viewing modality, the x-ray fluorescence microprobe and the at least one second imaging modality;
    b) producing a viewing image grid pattern by the viewing modality, a first image grid pattern by the x-ray fluorescence microprobe and at least one second image grid pattern by the at least one second imaging modality; and
    c) co-registering the viewing image grid pattern, the first image grid pattern and the at least one second image grid pattern.

10. The method of claim 9 wherein the marking grid is reflective metal.

11. The method of claim 9 wherein the marking grid is a reflective solid metal selected from the group consisting of gold, aluminum, chromium, and titanium.

12. The method of claim 9 wherein the reflective solid metal is gold or chromium.

13. The method of claim 9 wherein the marking grid is not a metal salt.

14. The method of claim 9 wherein the marking grid is a metal that does not interfere with the x-ray fluorescence microprobe or the at least one second imaging modality.

15. The method of claim 9 wherein one of the pattern thicknesses of the grid pattern generates a reflectivity as a function of the x-ray fluorescence microprobe and the at least one second imaging modality.

16. The method of claim 9 wherein one of the pattern thicknesses of the grid pattern generates a reflectivity sufficient to differentiate from the other of the at least two pattern thicknesses as a function of the x-ray fluorescence microprobe and the at least one second imaging modality.

17. The method of claim 9 wherein one of the at least two pattern thicknesses of the grid pattern is about 70% to about 90% reflective in the infrared region and the other of the at least two pattern thicknesses is about 100% reflective in the infrared region.

18. The method of claim 9 wherein one of the pattern thicknesses is about 85% reflective in the infrared region and the other of the at least two pattern thicknesses is at least about 100% reflective in the infrared region.

19. The method of claim 9 wherein the thin sample is biological.

20. The method of claim 19 further comprising the step of depositing the biological sample on the marking grid.

21. The method of claim 20 wherein the step of producing the first image grid pattern further comprises producing a first analytical image of the biological sample.

22. The method of claim 20 wherein the step of producing the at least one second image grid pattern further comprises producing at least one second analytical image of the biological sample.

23. The method of claim 20 wherein the biological sample contains a trace metal and organic matter.

24. The method of claim 23 wherein the trace metal is imageable by the x-ray fluorescence microprobe.

25. The method of claim 23 wherein the trace metal is zinc, iron, potassium, calcium, or copper.

26. The method of claim 25 wherein the marking grid is a metal that does not interfere with the trace metal.

27. The method of claim 26 wherein the marking grid is gold.

28. The method of claim 23 wherein the organic matter is imageable by the at least one second imaging modality.

29. The method of claim 28 wherein the second imaging modality is Fourier transform infrared microspectroscopy.

30. Method of viewing a first analytical image of a thin sample using an x-ray fluorescence microprobe having an x-ray beam that cannot be visualized by a light microscope objective comprising the steps of a) patterning a marking grid on a surface of a sample substrate, wherein said marking grid is imageable by the x-ray fluorescence microprobe and by the light microscope objective;
b) producing a first analytical image grid pattern by the x-ray fluorescence microprobe and a viewing image grid pattern by the light microscope objective; and
c) co-registering the first analytical image grid pattern and the viewing image grid pattern to correlate the viewing image with the x-ray beam of the x-ray fluorescence microprobe.

31. The method of claim 30 further comprising a second analytical image using a second imaging modality, wherein said marking is further imageable by the second imaging modality, comprising the further step of producing a second analytical image grid pattern by the second imaging modality and co-registering the second analytical image grid pattern with the first analytical image grid pattern and the viewing image grid pattern.

32. The method of claim 30 wherein the sample substrate is selected from the group consisting of glass, silicon, silicon nitride, mylar, kapton, polyethylene, and polypropylene.

33. The method of claim 30 wherein the sample substrate is a low trace element glass slide.

34. The method of claim 30 wherein the marking grid is metallic.

35. The method of claim 30 wherein the marking grid is a crossbar pattern.

36. The method of claim 30 wherein the step of co-registering further comprises overlaying the analytical image grid pattern and the viewing image grid pattern.

37. A fiducial marker used for correlating a first analytical image produced by a first analytical modality with a viewing image produced by a light microscope objective for analyzing a thin sample comprising
a) a sample substrate having a surface;
b) a marking grid having a grid pattern coated on the surface of the sample substrate, wherein the grid pattern (i) has a single layer pattern thickness, and (ii) is imageable by the x-ray fluorescence microprobe and the light microscope objective, and
c) wherein the x-ray beam cannot be visualized by the light microscope objective.

38. A fiducial marker used for correlating a first analytical image produced by an x-ray beam of an x-ray fluorescence microprobe and at least one second analytical image produced by at least one second imaging modality with a viewing image produced by a light microscope objective for analyzing a thin sample comprising
a) a sample substrate having a surface;
b) a marking grid having a grid pattern coated on the surface of the sample substrate, wherein the grid pattern (i) has at least two pattern thicknesses, and (ii) is imageable by the light microscope objective, by the first imaging modality and by the at least one second imaging modality,
c) wherein the x-ray beam cannot be visualized by the light microscope objective, and
d) wherein the first analytical image overlaps the at least one second analytical image.

* * * * *